United States Patent [19]

Maruyama et al.

[11] 4,281,001

[45] Jul. 28, 1981

[54] METHOD FOR TREATMENT OF RHEUMATISM

[75] Inventors: Yutaka Maruyama; Kazuhiro Goto; Michio Terazawa, all of Nakatsu, Japan

[73] Assignee: Yoshitomi Pharmaceutical Industries, Ltd., Osaka, Japan

[21] Appl. No.: 139,624

[22] Filed: Apr. 14, 1980

[30] Foreign Application Priority Data

Jan. 17, 1980 [JP] Japan ................................. 55-4161

[51] Int. Cl.$^3$ ............................................ A61K 31/435
[52] U.S. Cl. .................................................. 424/256
[58] Field of Search ......................................... 424/256

[56] References Cited

U.S. PATENT DOCUMENTS 4,085,111  4/1978  Oe et al. ................................. 546/89

Primary Examiner—Stanley J. Friedman
Attorney, Agent, or Firm—Sughrue, Rothwell, Mion, Zinn and Macpeak

[57] ABSTRACT

A method of treating rheumatism which comprises administration of 9-chloro-7-(1H-tetrazol-5-yl)-5-oxo-5H-[1H]benzopyrano[2,3-b]pyridine, and its salt and its hydrate.

4 Claims, No Drawings

METHOD FOR TREATMENT OF RHEUMATISM

This invention relates to a method of treating rheumatism in mammals, e.g. in humans which comprises administration of 9-chloro-7-(1H-tetrazol-5-yl)-5-oxo-5H-[1H]benzopyrano[2,3-b]pyridine and its salt (sodium salt, potassium salt, ammonium salt, diethylamine salt etc.).

The compound used in this invention is disclosed in U.S. Pat. No. 4,085,111 to be useful as antiallergic agent.

As a result of extensive investigations on other utility of the compound of this invention, the present inventors have found that the compound of this invention possesses a marked anti-rheumatic activity and this invention has thus been accomplished.

The compound of this invention is obtained by subjecting, e.g., 2-[2-chloro-4-(1H-tetrazol-5-yl)phenoxy]-nicotinic acid to ring formation reaction using sulfuric acid. Its sodium salt or its sodium salt pentahydrate have melting points higher than 300° C.

The active compound of the invention can be administered orally or parenterally per se or in the form of tablets, granules, powders, capsules, syrups, injectable solutions, suppositories, etc. in combination with a suitable and therapeutically acceptable carrier, vehicle, diluent, etc. The dose may vary depending upon the conditions to be treated, compound used, response to the medication, etc., but the daily dose for human adults usually ranges from about 10 mg to 1000 mg in single or multiple dose.

The following experiments illustrate that the active compound of the invention is useful as an antirheumatic agent. In these tests, 9-chloro-5-oxo-7-(1H-tetrazol-5-yl)-5H-[1]benzopyrano[2,3-b]pyridine sodium salt pentahydrate (mp.>300° C.; hereinafter referred to as Compound (I)) was used as test compound.

Experiment 1. Acute Toxicity

Compound (I) was administered orally or intraperitoneally to groups of eight male Wistar rats (about 200 g). Acute toxicity ($LD_{50}$ value) was calculated by the probit method after one week observation.

| Route | $LD_{50}$ |
| --- | --- |
| Oral | >16,000 mg/kg |
| Intraperitoneal | 7,778 mg/kg |

Similarly, acute toxicity of male dd-strain mice (20–25 g; ten per experimental group) was determined.

| Route | $LD_{50}$ |
| --- | --- |
| Oral | >16,000 mg/kg |
| Intraperitoneal | 9,278 mg/kg |

In these acute toxicities of rats and mice, differences between the sexes are not observed.

Experiment 2. Anti-adjuvant Arthritis Activity in Rats (A Model Disease of Rheumatoid Arthritis)

Male Wistar rats (8–9 week old) were used as test animals. Adjuvant arthritis was caused by the method of B. B. Newbould (Brit. J. Pharmacol. 21, 127 (1963)). Seventeen days after the subcutaneous injection of a suspension of killed tubercle bacillus in Freund's adjuvant into the foodpad of the left handpaw of the rat, the severity of arthritis was assayed as the hindleg volume and arthritic score. Each group of the rat was orally administered with Compound (I) in a dose and duration as shown in the table below. It was confirmed that the treatment with Compound (I) resulted in a significant inhibition of adjuvant arthritis in the rat. The significant inhibition in volume of injected leg was not observed on day 3 and 17 after the injection. Therefore, Compound (I) has no anti-inflammatory activity but does anti-arthritis activity.

| Days[1] drug administered | | −21 to +16 |
| --- | --- | --- |
| Dose (mg/kg/day) | | 50 |
| No. of rats/group | | 8 |
| Arthritis score[2] | | 60* |
| % Inhibition | Hindleg | Injected leg | 3 |
| | volume | Uninjected leg | 74* |

[1] Day after adjuvant injection.
[2] The lesion of the three paws and tail were each graded from 0 to 3. The lesion of the injected leg was not included.
*$P < 0.05$ significant vs. control.

Experiment 3. Activity against Antibody Production

BALB/C female mice of 6 weeks old were sensitized by intraperitoneally administering sheep blood red cells of $5 \times 10^8$. Compound (I) was given orally on the same day and next day of the sensitization. Blood was taken from the carotid artery on the fourth day after the antigen sensitization and blood serum was obtained. Measurement of blood serum agglutinin titer was carried out in accordance with the Waltz et al method (J. Pharmacol. Exp. Ther., 178, 223 (1971)) to determine 19S and 7S antibody titers.

As shown in the table below, Compound (I) inhibited the production of 19S antibody and accelerated the production of 7S antibody.

| Treatment | Dose (mg/kg) | Number of Animal | Serum Agglutinin Titer (log 2) | |
| --- | --- | --- | --- | --- |
| | | | 7S ± SE | 19S ± SE |
| Control | 0 | 6 | 2.0 ± 0 | 6.3 ± 0.3 |
| Compound (I) | 30 | 6 | 3.0 ± 0.3** | 5.1 ± 0.5* |

*$P < 0.05$
**$P < 0.01$ (significant difference as compared to control)

Next, activity on secondary immune response was examined after the administration of an antigen twice.

BALB/C female mice of 6 week old were sensitized by intraperitoneally administering sheep blood red cells of $5 \times 10^8$. Similar sensitization was performed further 21 days after. Blood was taken further 4 days after. In the aforesaid manner, 7S and 19S antibody titers in blood serum were measured. Compound (I) was orally administered on the day of the first sensitization and the following day. In this case, it was also found that the production of 19S antibody was inhibited, as shown in the table below, and the production of 7S antibody was promoted.

| Treatment | Dose (mg/kg) | Number of Animal | Serum Agglutinin Titer (log 2) | |
| --- | --- | --- | --- | --- |
| | | | 7S ± SE | 19S ± SE |
| Control | 0 | 6 | 7.5 ± 0.5 | 2.6 ± 0.2 |
| Compd. (I) | 0.3 | 6 | 9.1 ± 0.4* | 1.8 ± 0.1* |
| Compd. (I) | 3 | 6 | 9.0 ± 0.5* | 1.5 ± 0.1** |

-continued

| Treatment | Dose (mg/kg) | Number of Animal | Serum Agglutinin Titer (log 2) 7S ± SE | 19S ± SE |
|---|---|---|---|---|
| Compd. (I) | 30 | 6 | 9.1 ± 0.6* | 1.0 ± 0.3** |

*$P < 0.05$
**$P < 0.01$ (significant difference as compared to control)

Rheumatoid factor found in patient with chronic articular rheumatism belongs to immune globulins and is mainly composed of IgM (19S). It is said that IgM rheumatic factor would take major part in occurrence of arthritis. Accordingly, it is assumed that Compound (I) inhibiting the production of 19S antibody would prevent the production of IgM rheumatic factor of patient with chronic articular rheumatism and exhibit anti-rheumatic activity.

Experiment 4. Activity on Reticulo-endothelial System

In many cases, reticulo-endothelial function is reduced in patient with rheumatism (B. D. Williams et al, Lancet, 2, 1311 (1979)). Thus, the activity of Compound (I) on mice where reticulo-endothelial function was experimentally reduced was examined.

Using ICR/JCL male mice, reticulo-endothelial function was measured in accordance with the carbon clearance method of Halpern et al (Brit. J. Exp. Pathol., 34, 426 (1953)). The results are shown by phagocytic index (K) in a conventional manner.

| Treatment | Dose (mg/Kg) | Number of Animal | Phagocytic index (K) ± SE |
|---|---|---|---|
| Control | 0 | 13 | 0.0488 ± 0.0021** |
| Carrageenan | 50 (i.p.) | 12 | 0.0231 ± 0.0041 |
| Carrageenan + Compound (I) | 50 (i.p.) 30 (p.o.) | 10 | 0.0514 ± 0.0083** |

**$P < 0.01$ (significant difference as compared to carrageenan)

As is shown in the table, phagocytic index was significantly reduced when carrageenan was administered 24 hours before. This reduction was significantly recovered by simultaneous administration of Compound (I) with carrageenan. Accordingly, it is assumed that Compound (I) could recover reticulo-endothelial function which was reduced in patient with chronic arterial rheumatism.

As is also clear from the following clinical test, it is supported that the compound in accordance with the present invention is extremely excellent as an anti-rheumatic agent.

Clinical case: age of 53, female, right submaxilla articular rheumatism

The patient complained pain of the right submaxilla articular rheumatism and mouth-opening dysfunction due to pain on Jan. 27, 1978.

Prior to the administration of Compound (I), blood serum RA test was positive (++), and a slight increase of IgG FcR+ T cell ratio was noted. However, no particular abnormality was noted in blood pressure, electrocardiograph and general clinical tests.

Compound (I) was orally administered to the patient at the daily dose of about 240 mg consecutively for about 4 months (in combination with 3 tablets of a 25 mg dichlophenac sodium). After 1 month of the administration, Ra test was improved from ++ to + and at the same time, pain of the joint and mouth-opening dysfunction were also improved. Further, RA test conducted 6 months later showed negative. In addition, by the administration of Compound (I), increasing tendency of IgG, increase of lymphocyte ratio and reduction of IgG FcR+ T cell ratio were noted. No special abnormality in other liver function tests was observed. No side effect was noted, either.

As stated above, Compound (I) is useful for treatment of chronic articular rheumatism since it improves clinical symptoms of chronic articular rheumatism and tends to also improve various immunological parameters.

Pharmaceutical Preparation 1 (Tablets)

Pulverized Compound (I) (40 g), calcium carboxymethylcellulose (95.5 g), lactose (20 g), hydroxypropylcellulose (2 g), talc (2 g) and magnesium stearate (0.5 g) are thoroughly admixed, and the mixture is compressed on suitable punches to a tablet having a diameter of 7.5 mm and a weight of 160 mg.

Pharmaceutical Preparation 2 (Enteric Granules)

Compound (I) (25 g), lactose (29.2 g), calcium carboxymethylcellulose (13.6 g), polyvinylpyrrolidone (1.4 g) and hydroxypropylcellulose (0.6 g) are granulated by a conventional piston granulation (1 mm screen), and the granules are coated with a mixture of hydroxypropylmethylcellulose (14.5 g), methylacrylate-methacrylic acid copolymer (8 g) and castor oil (2.5 g) to form enteric cortical membrane.

Pharmaceutical Preparation 3 (Suppositories)

Compound (I) (40 mg), Witepsol $E_{75}$ (588 mg) and Witepsol $E_{15}$ (400 mg) are thoroughly admixed, and the mixture is filled up into a suppository container. ("Witepsol" is a Registered Trade Mark.)

What is claimed is:

1. A method of treating rheumatism in a mammal which comprises administration to said mammal which has rheumatism of an effective amount of 9-chloro-7-(1H-tetrazol-5-yl)-5-oxo-5H-[1H]benzopyrano-[2,3-b]pyridine, a pharmaceutically effective salt and a pharmaceutically effective hydrate thereof.

2. The method according to claim 1 which comprises administration of an effective amount of 9-chloro-7-(1H-tetrazol-5-yl)-5-oxo-5H-[1H]benzopyrano[2,3-b]pyridine sodium salt pentahydrate.

3. The method according to claim 1 which comprises administration of an effective amount of 9-chloro-7-(1H-tetrazol-5-yl)-5-oxo-5H-[1H]benzopyrano[2,3-b]pyridine.

4. The method of claim 1 wherein said pharmaceutically effective salt is selected from the group consisting of the sodium salt, potassium salt, ammonium salt and diethylamine salt thereof.

* * * * *